United States Patent [19]
Yoon

[11] Patent Number: 5,637,097
[45] Date of Patent: Jun. 10, 1997

[54] PENETRATING INSTRUMENT HAVING AN EXPANDABLE ANCHORING PORTION

[76] Inventor: InBae Yoon, 2101 Highland Ridge Dr., Phoenix, Md. 21131

[21] Appl. No.: 433,904

[22] Filed: May 2, 1995

Related U.S. Application Data

[60] Continuation-in-part of Ser. No. 79,586, Jun. 22, 1993, Pat. No. 5,423,770, which is a division of Ser. No. 868,578, Apr. 15, 1992, Pat. No. 5,336,176.

[51] Int. Cl.$^6$ .................................. A61B 17/34
[52] U.S. Cl. ..................... 604/174; 604/104; 604/164; 604/165; 604/175; 604/178
[58] Field of Search .................... 604/104, 164, 604/165, 174, 175, 178

[56] References Cited

U.S. PATENT DOCUMENTS

| | | |
|---|---|---|
| 4,393,873 | 7/1983 | Nawash et al. . |
| 4,608,965 | 9/1986 | Anspach, Jr. et al. . |
| 4,654,030 | 3/1987 | Moll et al. .................... 604/165 |
| 4,846,784 | 7/1989 | Haber .......................... 600/29 |
| 5,030,206 | 7/1991 | Lander ......................... 604/164 |
| 5,104,382 | 4/1992 | Brinkerhoff et al. ............. 604/165 |
| 5,122,122 | 6/1992 | Allgood . |
| 5,147,316 | 9/1992 | Castillenti . |
| 5,183,033 | 2/1993 | Wilk . |
| 5,203,773 | 4/1993 | Green . |
| 5,217,451 | 6/1993 | Freitas . |
| 5,232,440 | 8/1993 | Wilk . |
| 5,248,302 | 9/1993 | Patrick et al. . |
| 5,257,975 | 11/1993 | Foshee . |
| 5,282,788 | 2/1994 | Wilk et al. . |
| 5,290,243 | 3/1994 | Chodorow et al. ............... 604/165 |
| 5,290,249 | 3/1994 | Foster et al. ................... 604/174 |
| 5,312,354 | 5/1994 | Allen et al. .................... 604/157 |
| 5,318,012 | 6/1994 | Wilk . |
| 5,318,580 | 6/1994 | Gresl, Jr. ...................... 606/185 |
| 5,330,497 | 7/1994 | Freitas et al. .................. 606/185 |
| 5,387,196 | 2/1995 | Green et al. . |
| 5,387,197 | 2/1995 | Smith et al. ................... 604/164 |
| 5,486,190 | 1/1996 | Green ........................... 606/184 |

*Primary Examiner*—Sam Rimell
*Assistant Examiner*—Robert V. Racunas

[57] ABSTRACT

A penetrating instrument for penetrating a wall of an anatomical cavity to gain access to the anatomical cavity includes a fixed or retractable penetrating member having a distal end for penetrating the anatomical cavity wall, a portal sleeve fixed relative to the penetrating member or movable between an extended position protecting the distal end of the penetrating member and a retracted position exposing the distal end of the penetrating member, and an expandable portion carried by the portal sleeve and movable from an expanded position to a contracted position during penetration of the cavity wall and from the contracted position to the expanded position upon introduction of the expandable portion in the anatomical cavity to anchor the portal sleeve relative to the anatomical cavity wall.

19 Claims, 8 Drawing Sheets

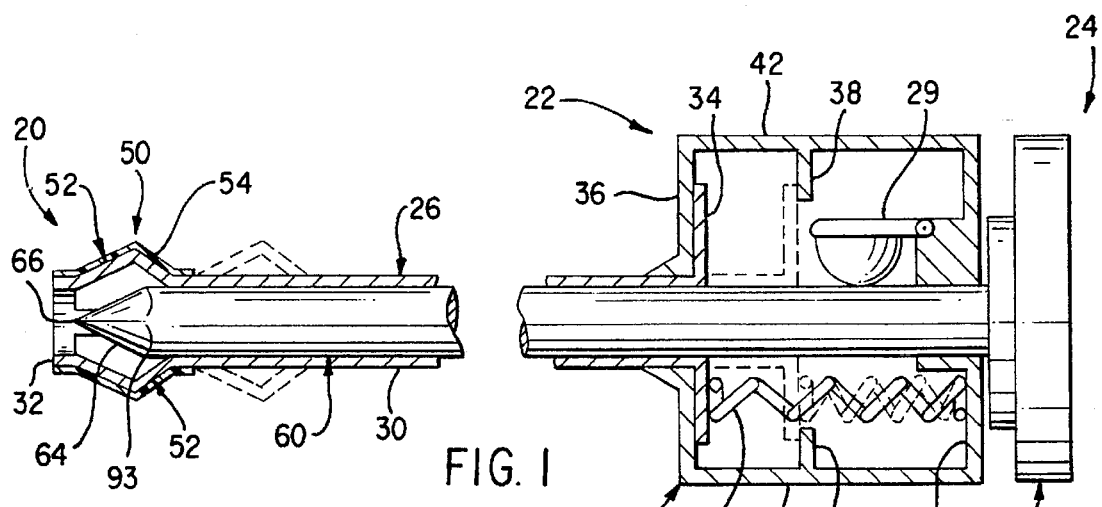
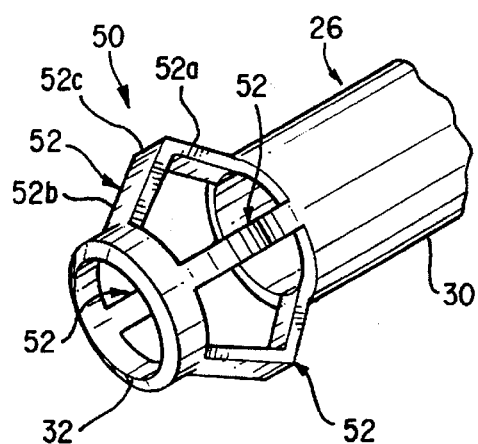
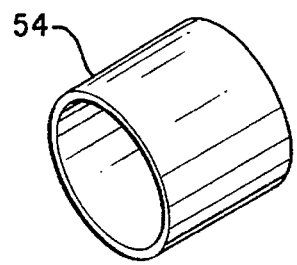
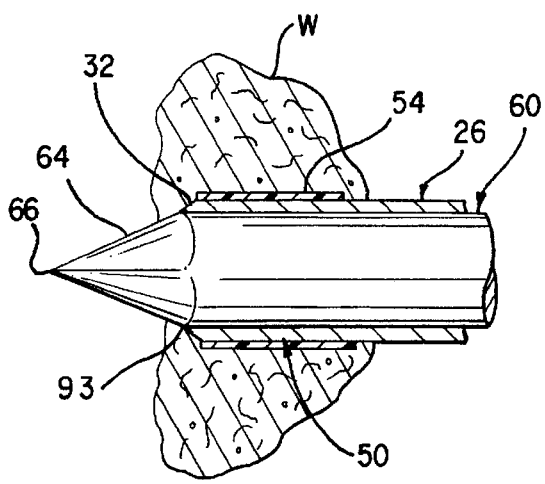 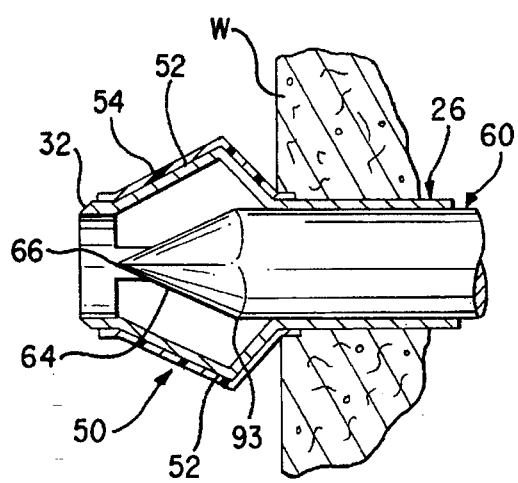

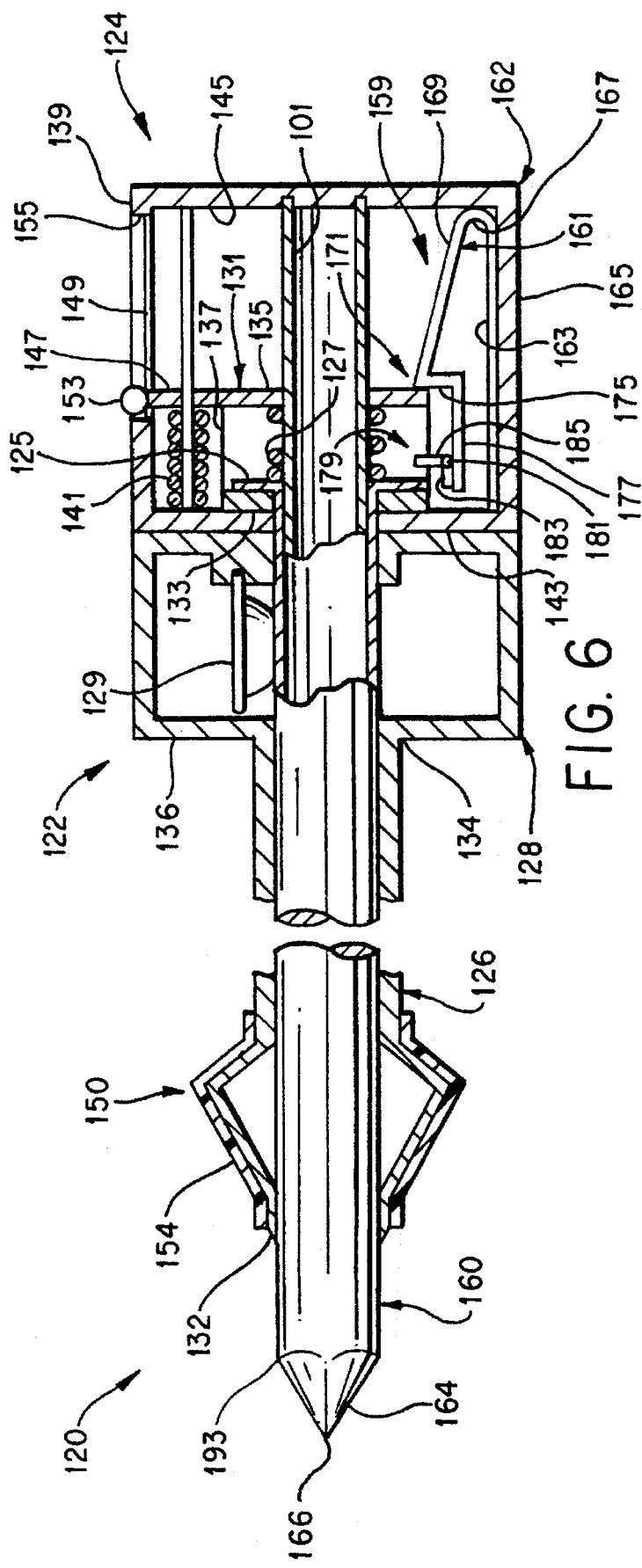

PENETRATING INSTRUMENT HAVING AN EXPANDABLE ANCHORING PORTION

CROSS-REFERENCE TO RELATED APPLICATIONS

This application is a continuation-in-part of application Ser. No. 08/079,586, filed Jun. 22, 1993, now U.S. Pat. No. 5,423,770, which is a division of application Ser. No. 07/868,578, filed Apr. 15, 1992, now U.S. Pat. No. 5,336,176, the disclosures of which are incorporated herein by reference.

BACKGROUND OF THE INVENTION

1. Field of the Invention

The present invention pertains to penetrating instruments for penetrating walls of anatomical cavities and, more particularly, to penetrating instruments having retractable penetrating members and/or safety members biased to an extended protruding position such that tissue and organ structures are protected from the tips of the penetrating members. The present invention also pertains to penetrating instruments having anchoring members to automatically anchor the penetrating instruments upon penetration into anatomical cavities.

2. Discussion of the Prior Art

Penetrating instruments are widely used in medical procedures to gain access to anatomical cavities ranging in size from the abdomen to small blood vessels, such as veins and arteries, epidural, pleural and subarachnoid spaces, heart ventricles and spinal and synovial cavities. Use of penetrating instruments has become an extremely popular and important first step in endoscopic, or minimally invasive, surgery to establish an endoscopic portal for many various procedures, such as laproscopic procedures in the abdominal cavity. Such penetrating instruments typically include a cannula or portal sleeve and a penetrating member, such as a trocar, disposed within the cannula and having a sharp tip for penetrating an anatomical cavity wall with the force required to penetrate the cavity wall being dependent upon the type and thickness of the tissue forming the cavity wall. Once the wall is penetrated, it is desirable to protect the sharp tip of the penetrating member from inadvertent contact with or injury to tissue or organ structures in or forming the cavity in that, once penetration is achieved, the lack of tissue resistance can result in the sharp tip traveling too far into the cavity and injuring adjacent tissue or organ structures.

Various safety penetrating instruments have been proposed, generally falling into protruding and retracting categories. In protruding safety penetrating instruments, a safety member is spring-biased to protrude axially beyond the tip of the penetrating member in response to the reduced force on the distal end of the safety member upon entry into the anatomical cavity. The safety member can be disposed around the penetrating member in which case the safety member is frequently referred to as a shield, or the safety member can be disposed within the penetrating member in which case the safety member is frequently referred to as a probe. In retracting safety penetrating instruments, the penetrating member is retracted into the cannula upon entry into the anatomical cavity in response to distal movement of a component of the safety penetrating instrument such as the penetrating member, the cannula, a probe or a safety member such as a shield or probe.

While safety penetrating instruments have been well received, there is room for improvement in easing penetration and minimizing the likelihood of a safety member being extended or a penetrating member being retracted before the cannula has entered the anatomical cavity in that distal movement of a triggering component of the safety penetrating instrument can be induced prematurely if the axial penetrating force applied by the surgeon is irregular or uneven.

Penetrating instruments for establishing communication with anatomical cavities in many various medical procedures and having anchoring members for anchoring the penetrating instruments relative to the anatomical cavities have also been proposed. However, there is room for improvement in this area as well due to the need for intervention by the surgeon to actuate the anchoring members upon penetration into the anatomical cavities.

SUMMARY OF THE INVENTION

Accordingly, it is a primary object of the present invention to improve penetrating instruments of the type having anchoring members for anchoring the penetrating instruments upon penetration by the penetrating instruments into anatomical cavities.

Another object of the present invention is to utilize an expandable portion of a penetrating instrument as an anchoring member for anchoring the penetrating instrument relative to an anatomical cavity wall upon penetration of the penetrating instrument into the anatomical cavity.

A further object of the present invention is to carry or form an expandable member on a penetrating instrument and permit movement of the expandable portion from an expanded position to a contracted position automatically in response to resistance from anatomical tissue during penetration and from the contracted position to the expanded position upon introduction of the expandable portion in the anatomical cavity.

The present invention has as an additional object to ease penetration of an anatomical cavity wall with a penetrating instrument by carrying or forming an expandable portion on a cannula of the penetrating instrument and permitting the expandable portion of the cannula to axially extend in a distal direction when moved from an expanded position to a contracted position in order to align a distal end of the cannula with a distal end of a penetrating member of the penetrating instrument.

Some of the advantages of the present invention are that anchoring of a penetrating instrument relative to an anatomical cavity wall can be achieved without the need for intervention by the surgeon to actuate the anchoring member upon penetration into the anatomical cavity, that movement of a safety member to the extended protruding position and/or retraction of a penetrating member, as well as automatic anchoring of the penetrating instrument, can be accomplished simultaneously and that the penetrating instrument of the present invention can be inexpensively manufactured with minimum components to reduce cost, facilitate sterilization for re-use and allow economical, single patient use.

The present invention is generally characterized in a penetrating instrument for penetrating an anatomical cavity wall to gain access to an anatomical cavity including a cannula having a distal end for being disposed in the anatomical cavity and a proximal end for being disposed externally of the anatomical cavity, a penetrating member disposed in the cannula and having a distal end for penetrating the anatomical cavity wall, and an expandable portion disposed along the cannula a predetermined distance from the cannula distal end, the expandable portion being biased outwardly in a lateral direction transverse to a longitudinal axis of the cannula to an expanded position and being movable to a contracted position against the bias in response to tissue resistance during penetration of the anatomical cavity wall, the expandable portion further being movable from the contracted position to the expanded position in response to a reduction in tissue resistance upon introduction of the expandable portion in the anatomical cavity. In the expanded position, the expandable portion has a configuration to anchor the cannula to protrude into the anatomical cavity a distance corresponding to the predetermined distance.

The above and still further objects, features and advantages of the present invention will become apparent from the following description of the preferred embodiments when considered in conjunction with the accompanying drawings wherein, unless otherwise specified, like reference numerals or reference numerals sharing the same last two digits are utilized to designate like components in the various figures.

BRIEF DESCRIPTION OF THE DRAWINGS

FIG. 1 is a broken side view, partly in section, of a penetrating instrument according to the present invention.

FIG. 2 is a fragmentary perspective view of a distal end of the portal sleeve for the penetrating instrument of FIG. 1.

FIG. 3 is a perspective view of a membrane to be disposed over the expandable portion of the penetrating instrument of FIG. 1.

FIG. 4 is a fragmentary side view, partly in section, of the penetrating instrument of FIG. 1 during penetration of a wall of an anatomical cavity.

FIG. 5 is a fragmentary side view, partly in section, of the penetrating instrument of FIG. 1 following entry in the anatomical cavity.

FIG. 6 is a broken side view, partly in section, of a modification of the penetrating instrument according to the present invention.

DESCRIPTION OF THE PREFERRED EMBODIMENTS

Figure 7:
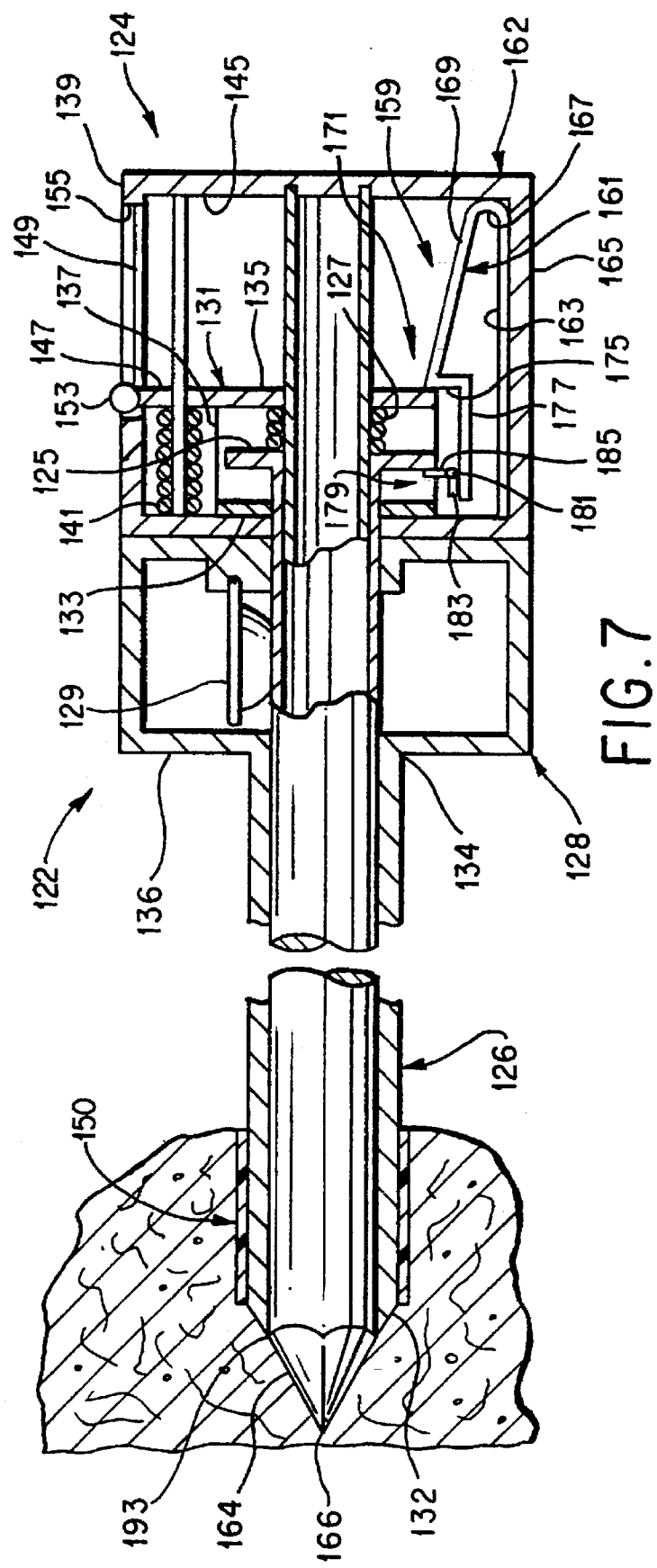
FIG. 7 is a broken side view, partly in section, of the penetrating instrument of FIG. 6 during penetration of a wall of an anatomical cavity.

The penetrating instrument of the present invention is described hereinafter for use as an instrument for inserting a portal sleeve through a wall of an anatomical cavity to form a portal for the introduction of various surgical and diagnostic instruments into the cavity during endoscopic procedures, such as laparoscopy. It is understood, however, that the penetrating instrument of the present invention can be used for penetration or introduction into anatomical cavities of needles with fluid flow therethrough and catheters as well as for other instruments engaging tissue during surgical or diagnostic procedures. Accordingly, the cannula or outer tubular member of the penetrating instrument can be a portal sleeve, a needle, a catheter or a tubular component of a medical instrument.

A penetrating instrument 20 according to the present invention, as shown in FIG. 1, is formed of a portal unit 22 and a penetrating unit 24. The portal unit 22 includes an elongate portal sleeve, cannula or catheter 26 and a housing 28 mounting a proximal end of the portal sleeve. Housing 28 can have any configuration in cross-section to facilitate grasping by a surgeon and is preferably constructed to sealingly engage instruments passing therethrough and to include a valve 29 biased to a closed state when no instrument passes through the portal sleeve. Valve 29 is shown as a flapper valve; however, any suitable valve construction can be utilized including, for example, trumpet or nipple valves. Portal sleeve 26 defines a lumen for receiving a penetrating member of penetrating unit 24 and is made up of a body 30 terminating distally at a distal end 32 and proximally at a flange 34 disposed between a front wall 36 of housing 28 and a pair of transverse interior walls 38 and 40 depending from top and bottom walls 42 and 44, respectively, of the housing to serve as stops or abutments limiting proximal movement of the portal sleeve. Body 30 can be cylindrical, tubular or have any other desirable configuration in cross-section in accordance with the procedure to be performed and the anatomical cavity to be penetrated. A bias member 46 is connected between flange 34 and a wall or other structure of housing 28 to bias the portal sleeve in a distal direction relative to the housing so that flange 34 normally abuts housing front wall 36. Bias member 46 can include a helical coil spring mounted in compression between flange 38 and a rear wall 48 of housing 28 as shown or any other type of spring or other bias device including tension springs, compression springs, torsion springs, pan springs, pivotally connected members, rubber, plastic or magnets, for example.

Portal sleeve 26 also includes an expandable portion 50 proximally spaced from the portal sleeve distal end a predetermined distance corresponding to a desired amount of protrusion of the portal sleeve into an anatomical cavity following penetration. As shown in FIG. 2, expandable portion 50 includes one or more longitudinally extending legs or strips 52 having opposing ends flexibly or pivotally connected to the portal sleeve. Strips 52 are each formed of straight segments 52a and 52b flexibly or pivotally connected at joints, pivots or hinges 52c. The expandable portion 50 is biased to the expanded position where the straight segments 52a and 52b are pivoted relative to one another along the pivots 52c to form an angular configuration. The segments 52a and 52b and the pivots 52c can be made as separate components or can be of integral one-piece construction. In the expanded position for expandable portion 50, the pivots 52c are disposed outwardly of the periphery of body 30 of the portal sleeve with segment 52a angled proximally and segment 52b angled distally. In the contracted position, the segments 52a and 52b will be longitudinally axially aligned or substantially longitudinally axially aligned parallel or in alignment with or substantially parallel or in alignment with the longitudinal axis of the instrument. In the expanded position, strips 52 form an enlargement or protrusion along portal sleeve 26 having a configuration to anchor the instrument 20 relative to an anatomical cavity.

The outward bias for expandable portion 50 can be selected to permit movement of the expandable portion inwardly toward the instrument longitudinal axis in the radial or transverse direction from the expanded position to the contracted position shown in FIG. 4 in response to resistance or force from anatomical tissue during penetration of an anatomical cavity wall and to permit movement of the expandable portion outwardly in the radial or transverse direction from the contracted position to the expanded position in response to a decrease, reduction or removal of the resistance or force upon penetration into the cavity. In the contracted position, strips 52 are flattened or straightened to be disposed parallel or in alignment with or substantially parallel or in alignment with the longitudinal axis of the instrument such that the expandable portion 50 has an axial length in the contracted position greater than the axial length of the expandable portion 50 in the expanded position. Accordingly, movement of expandable portion 50 from the expanded to the contracted position causes the distal end of portal sleeve 26 to move distally relative to the penetrating member, and movement of expandable portion 50 from the contracted position to the expanded position causes the distal end of the portal sleeve to move proximally relative to the penetrating member. Additionally, in the contracted position, the periphery, circumference or cross-section of the expandable portion 50 is aligned or substantially aligned with the periphery, circumference or cross-section of portal sleeve 26 to facilitate passage of the portal sleeve through the anatomical tissue.

The longitudinal distance from a distal end of the portal unit to a proximal end of the expandable portion 50 in the expanded position can be selected in accordance with the amount of protrusion into the anatomical cavity desired for the portal unit; and, therefore, the location of the expandable portion 50 along the instrument 20 can be selected in accordance with the amount of protrusion into the anatomical cavity desired for the portal unit. As shown in FIG. 1, the distance from the portal sleeve distal end 32 to a proximal end of expandable portion 50 in the expanded position is selected to obtain a predetermined amount of protrusion of the portal sleeve 26 into the anatomical cavity following penetration. Accordingly, the expandable portion 50 can be provided along the penetrating instrument at various distances from the portal unit distal end, in accordance with the amount of protrusion into the anatomical cavity desired for the portal unit; and the expandable portion can be located to obtain various predetermined amounts of protrusion for various procedures. It will be appreciated, therefore, that expandable portion 50 is illustrated herein adjacent a distal end of the portal sleeve by way of example only.

The outward bias for expandable portion 50 can be provided in many various ways such as by forming strips 52 of a resilient spring material or a material having shape memory, such that the outward bias is provided by the strips themselves, or by utilizing a separate bias device, such as spring wire, embedded within or otherwise mounted on the strips.

FIG. 3 illustrates a stretchable, flexible, deformable, resilient or elastic membrane or sheath 54 to be disposed over expandable portion 50. Membrane 54 can have a tubular or cylindrical cross-section as shown or any other desired configuration in cross-section to cover expandable portion 50 in the expanded and contracted positions. Membrane 54 can be disposed over the portal sleeve 26 as shown, or the membrane can be disposed between the portal sleeve 26 and the penetrating member. The membrane 54 can be secured with adhesive or made to fit snugly or tightly over the portal sleeve. The membrane 54 can be made of any suitable stretchable, flexible, resilient, deformable or elastic medical grade material, such as silicone rubber or sponge, to conform or stretch to the configuration and size of the expandable portion 50 in the expanded position. Where the membrane 54 is disposed between the portal sleeve and the penetrating member, the membrane will be pulled by the strips 52. The membrane 54 can have a length to cover portion 50 and can extend to the distal end of the portal unit.

The penetrating unit 24 includes an elongate penetrating member 60 for being received in the lumen of portal sleeve 26 and having a proximal end mounted by a hub 62, a distal end 64 tapering inward from a junction 93 to a sharp tip or point 66 and a shaft or body extending between the proximal and distal ends. The distal end can have any configuration desired by a surgeon for a particular procedure such as, for example, the pyramidal trocar configuration shown or conical, threaded, multifaceted or open, slanted or needle configurations. The penetrating member 60 can be made of any suitable, medical grade materials and can be made of multiple components such that, for example, the distal end can be made of stainless steel and secured in any conventional manner, such as by threads, to the distal end of the shaft, which can be tubular and made of a less expensive material, such as plastic or metal. The hub 62 can have any desired external configuration to facilitate grasping of the portal unit and the penetrating unit by the surgeon with one hand.

The portal unit 22 and the penetrating unit 24 can be provided to a surgeon separately or assembled together as shown in FIG. 1, and either or both of the portal and penetrating units can be manufactured in a manner to be disposable for single patient use or to be sterilizable for re-use. The hub 62 can be coupled to the housing 28 by suitable detent or latch mechanisms if desired, and the penetrating unit 24 can be withdrawn from the portal unit 22 leaving the portal sleeve 26 in place within an anatomical cavity.

In use, when a surgeon desires to penetrate into an anatomical cavity using the penetrating instrument 20, the instrument is in the condition shown in FIG. 1 with expandable portion 50 in the expanded position and portal sleeve 26 in the extended position where flange 34 abuts housing front wall 36 and portal sleeve distal end 32 protrudes distally beyond the sharp tip 66 of the penetrating member. When the distal end 32 of the portal sleeve is brought into contact with tissue forming an anatomical cavity wall W, the portal sleeve 26 is moved longitudinally in the proximal direction against the bias of bias member 46 toward a retracted position where flange 34 of the portal sleeve abuts interior walls 38 and 40 as shown by dotted line in FIG. 1 and the sharp tip 66 of the penetrating member is exposed. As penetration continues, sharp tip 66 of the penetrating member is made to penetrate into the anatomical cavity wall and distally angled segments 52b of expandable portion 50 are forced into contact with the anatomical tissue surrounding the opening formed by the penetrating member. As expandable portion 50 is advanced into the opening, segments 52b are cammed inwardly in a lateral direction transverse to a longitudinal axis of the instrument in response to the force from tissue contact. Segments 52b pivot inwardly about pivots 52c thereby drawing proximally angled segments 52b inwardly as well.

Expandable portion 50 of the portal sleeve 26 is thus compressed, collapsed or contracted inwardly as the penetrating instrument is advanced through the anatomical cavity wall causing movement of the expandable portion 50 from the expanded position to the contracted position as shown in FIG. 4 to facilitate movement of portal sleeve 26 through the anatomical cavity wall. Movement of expandable portion 50 from the expanded position to the contracted position also causes longitudinal distal movement of portal sleeve distal end 32 relative to penetrating member 60 such that the distal end 32 of the portal sleeve becomes aligned with the junction 93 between the body of the penetrating member and the penetrating member distal end to provide a smooth distal profile easing penetration.

Once expandable portion 50 has passed through the anatomical cavity wall W, the force from tissue contact will be reduced, decreased or removed causing expandable portion 50 to move from the contracted position to the expanded position due to the bias of strips 52 as shown in FIG. 5 to anchor the instrument 20 relative to the anatomical cavity wall. At about the same time, bias member 46 moves the portal sleeve 26 to the extended position where distal end 32 of the portal sleeve is disposed distally beyond the sharp tip of the penetrating member 60. With the expandable portion 50 in the expanded position, the portal sleeve 26 will be anchored in the anatomical cavity and will protrude from the cavity wall into the anatomical cavity a predetermined distance corresponding to the position of the expandable portion 50. The penetrating unit 24 can be withdrawn from the portal unit 22 leaving the portal sleeve in place such that instruments for performing endoscopic procedures can be introduced into the cavity via the portal formed by the portal unit.

Many various procedures can be conducted via the portal sleeve 26 with greater security in that the expandable portion 50 prevents inadvertent backing out of the portal sleeve from the anatomical cavity wall. Upon completion of the procedures, the portal sleeve can be withdrawn from the anatomical cavity with a manual force sufficient to cause the portion 50 to be moved to the contracted position, and removal of the portal sleeve can be facilitated by providing a proximal end of the portion 50 with a distal angle or slope as shown.

It will be appreciated that the expandable portion 50 can be designed in many various ways in addition to the strips shown herein; for example, the expandable portion can include various springs, including coil springs, as well as inflatable membranes, and the expandable portion can be used with or without the protective membrane or sheath. It will further be appreciated that the expandable portion can be designed to be moved manually between the expanded and contracted positions during use rather than or in addition to being moved automatically in response to a force from anatomical tissue.

A modification of the penetrating instrument according to the present invention is shown in FIG. 6 at 120 wherein the proximal end 134 of the portal sleeve 126 is fixed to the front wall 136 of the housing 128 and the penetrating member 160 is movable between an extended position where a distal end of the penetrating member protrudes distally beyond the distal end of the portal sleeve and a retracted position where the distal end of the penetrating member is proximally spaced from the distal end of the portal sleeve. Portal unit 122 for penetrating instrument 120 is similar to portal unit 22 for penetrating unit 20 in that it includes a portal sleeve 126 having a distal end 132, a proximal end 134 and an expandable portion 150; however, unlike portal sleeve 26, the proximal end of portal sleeve 126 is fixed relative to the housing so that the distal end of the portal sleeve moves only in response to movement of expandable portion 150 between expanded and contracted positions.

Penetrating unit 124 is similar to penetrating unit 24 and includes a hub 162 mounting a proximal end of a penetrating member 160 similar to penetrating member 60 of penetrating instrument 20 but with a hollow proximal portion telescopically fitted over a guide tube 101 extending from rear wall 145 of the hub. A flange 125 at the proximal end of the penetrating member is disposed within a U-shaped rail member 131 in the hub; and, as shown in FIG. 6, rail member 131 includes a forward wall 133 disposed transverse or perpendicular to a longitudinal axis of the penetrating instrument 120 and parallel or substantially parallel to flange 125, a rearward wall 135 spaced from and parallel to forward wall 133 and a side wall 137 transversely joining the forward and rearward walls. Rearward wall 135 extends toward an upper wall 139 of hub 162, and a retracting member 141 is mounted between the rail member rearward wall 135 and a front wall 143 of hub 162 to bias the penetrating member 160 in a proximal direction to a safe, retracted position where distal end 164 of the penetrating member is disposed proximally of the portal sleeve distal end 132. The retracting member 141 can include a helical coil spring mounted in compression between rail member rearward wall 135 and the hub front wall 143 as shown or any other type of spring or other bias device including tension springs, compression springs, torsion springs, pan springs, pivotally connected members, rubber, plastic or magnets, for example. If desired, a guide rod can be connected between front wall 143 and the rear wall 145 of hub 162 with the spring 141 disposed around the guide rod.

Penetrating member 160 extends through an opening in the rail member forward wall 133 to terminate proximally at flange 125, and a bias member 127 is connected between the flange and rail member to bias the penetrating member in a distal direction relative to the rail member. Bias member 127 can include a helical coil spring mounted in compression between flange 125 and rail member rearward wall 135 as shown or any other type of spring or bias device as described above.

A pin 147 extends from rail member rearward wall 135 through a slot 149 in upper wall 139 of the hub to terminate at a handle or knob 153 positioned in an elongate, trough-like recess 155 in the upper wall. Slot 149 and recess 155 extend longitudinally in parallel with the longitudinal axis of the penetrating instrument 120.

Hub 162 mounts a locking and releasing mechanism 159 for locking the penetrating member 160 in an extended position exposing the sharp distal tip 166 of the penetrating member and for releasing the penetrating member to allow the penetrating member to move proximally to the retracted position. Locking and releasing mechanism 159 includes a latch or locking spring 161, made of a strip of resilient material, formed to have a substantially flat base 163 secured to lower wall 165 of hub 162 or to a structure within the hub and a bend 167 joining the proximal end of the base 163 with an upwardly angled arm 169 spaced from the base. Arm 169 carries or forms a latch 171 having a proximal angled latching surface joining a distal angled latching surface 175 disposed substantially transverse to the longitudinal axis of the penetrating instrument and substantially parallel to the rail member rearward wall 135. Arm 169 has an extension 177 extending perpendicularly from latch 171 in a distal direction, and a releasing or trigger member 179 is juxtaposed with extension 177. The trigger 179 is pivotally mounted in the hub on a pin 181 secured to a wall or walls of the hub or structure supported in the hub, and the trigger is generally L-shaped with a leg 183 overlying extension 177 and a leg 185 extending substantially transversely from leg 183 but at a slight angle toward the proximal end of the safety penetrating instrument. A torsion spring (not shown) is coiled around pin 181 and fixed to trigger 179 to bias the trigger counterclockwise looking at FIG. 6 such that leg 183 is biased toward extension 177.

Figure 8:
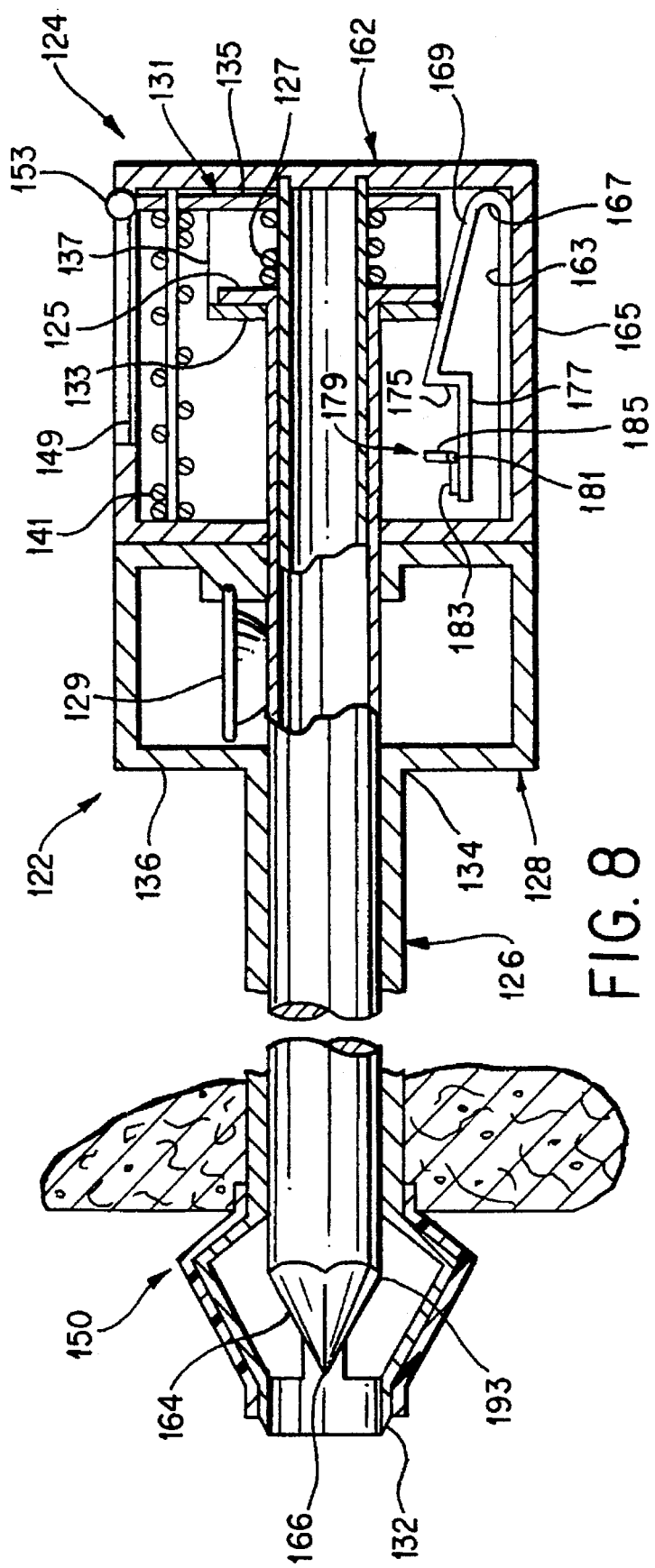
FIG. 8 is a broken side view, partly in section, of the penetrating instrument of FIG. 6 following entry in the anatomical cavity.

In use, the safety penetrating instrument 120 will normally be provided in the condition illustrated in FIG. 8 with the expandable portion 150 in the expanded position and the penetrating member 160 in the retracted position where the sharp distal tip 166 of the penetrating member is covered or protected. With the safety penetrating instrument 120 in the condition shown in FIG. 8, flange 125 will be in abutment with the forward wall 133 of rail member 131 due to the bias of bias member 127, and handle 153 will be disposed at a proximal end of slot 149. Prior to commencing penetration of an anatomical wall W, handle 153 is grasped and manually moved distally to move penetrating member 160 distally against the bias of retracting member 141 until rail member rearward wall 135 rides over latch 171 by engaging the proximal latching surface to move arm 169 toward base 163. At this time, the surgeon can feel the rail member lock into place with the rail member rearward wall 135 in engagement with distal latching surface 175 as arm 169 springs back and can also visually determine that the portal sleeve is locked in the retracted position by noting the position of handle 153 at a distal end of slot 149.

The penetrating instrument 120 is now in the position illustrated in FIG. 6 with penetrating member 160 locked in the extended position by locking and releasing mechanism 159 and expandable portion 150 in the expanded position. In the locked or extended position, the operating member formed by flange 125 of the penetrating member is biased into abutment with rail member forward wall 133 and is therefore disposed distally of trigger leg 185. Also, with penetrating member 160 in the extended position and flange 125 abutting rail member forward wall 133, portal sleeve distal end 132 is proximally spaced from the penetrating member distal end junction 193 a predetermined distance corresponding approximately to the sum of the distance between rail member walls and the amount of axial extension of expandable portion 150 so that, when the penetrating member is moved proximally relative to the rail member and the expandable portion is moved from the expanded position to the contracted position, portal sleeve distal end 132 will be aligned with the rear edge or junction 193 of the penetrating member distal end 164.

As penetration of the anatomical cavity wall W is commenced, the force-to-penetrate is limited to the force required to cause the penetrating member to move proximally within rail member 131 and the sharp distal end 166 to pass through the cavity wall W since the portal sleeve does not move longitudinally during penetration. Movement of penetrating member 160 in the proximal direction during penetration of the anatomical cavity wall W causes the operating member formed by flange 125 to move proximally until flange 125 abuts the rearward wall 135 of rail member 131 which serves as a stop or abutment limiting proximal movement of the operating member. As the flange 125 moves proximally, the operating member formed thereby engages trigger leg 185 to pivot trigger 179 clockwise, looking at FIG. 7, allowing the operating member to pass thereby. The clockwise pivotal movement of trigger 179 does not cause movement of the latch 171 since there is no engagement by either leg 183 or leg 185 with arm extension 177. As penetration continues, the penetrating instrument will advance through the cavity wall W as shown in FIG. 7, and the force from tissue contact with expandable portion 150 will cause the expandable portion to be moved from the expanded position to the contracted position thereby axially extending the portal sleeve distal end 132 into axial alignment with the penetrating member distal end junction 193 such that passage of the portal sleeve through the anatomical cavity wall is facilitated.

Figure 11:
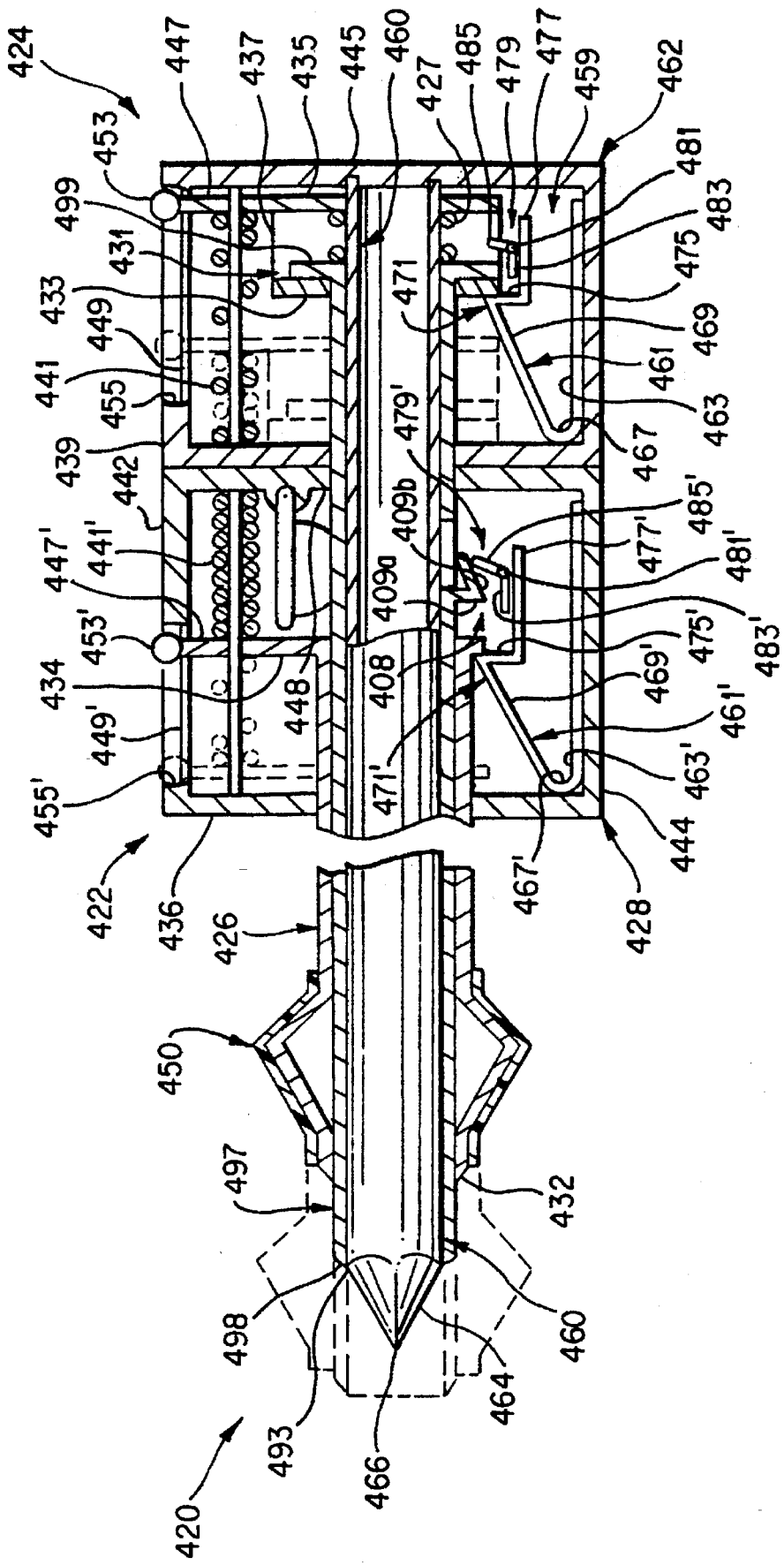
FIG. 11 is a broken side view, partly in section, of still another modification of the penetrating instrument according to the present invention.

When the penetrating member 160 enters the anatomical cavity, the reduction in force from tissue contact with the distal end of the penetrating member permits bias member 127 to move the penetrating member, and thus flange 125, distally relative to rail member 131. The operating member formed by flange 125 is thus made to engage leg 185 of trigger member 179 causing the trigger member to pivot counterclockwise looking at FIG. 7 and causing leg 183 to engage arm extension 177 moving arm 169 toward base 163 against the force of spring strip 161. The movement of arm 169 away from the longitudinal axis of the safety penetrating instrument causes latch 171 to move out of engagement with rail member rearward wall 135 thereby allowing retracting member 141 to move the penetrating member proximally to the retracted position as illustrated in FIG. 11. At about the same time, expandable portion 150 will enter the anatomical cavity and, as a result of the reduction in force from tissue contact, the expandable portion 150 will be returned to the expanded position within the anatomical cavity. Once portion 150 has moved from the contracted position to the expanded position upon penetration into the anatomical cavity, the instrument can be pulled back toward the cavity wall until the enlargement formed by the expandable portion 150 is adjacent or in abutment with an internal surface of the cavity wall at which time the portal sleeve will be anchored relative to the anatomical cavity wall to prevent backing out of the portal sleeve from the anatomical cavity. The portal sleeve will be anchored to protrude into the anatomical cavity a distance corresponding to the distance from the portal sleeve distal end to a proximal end of expandable portion 150.

Figure 9:
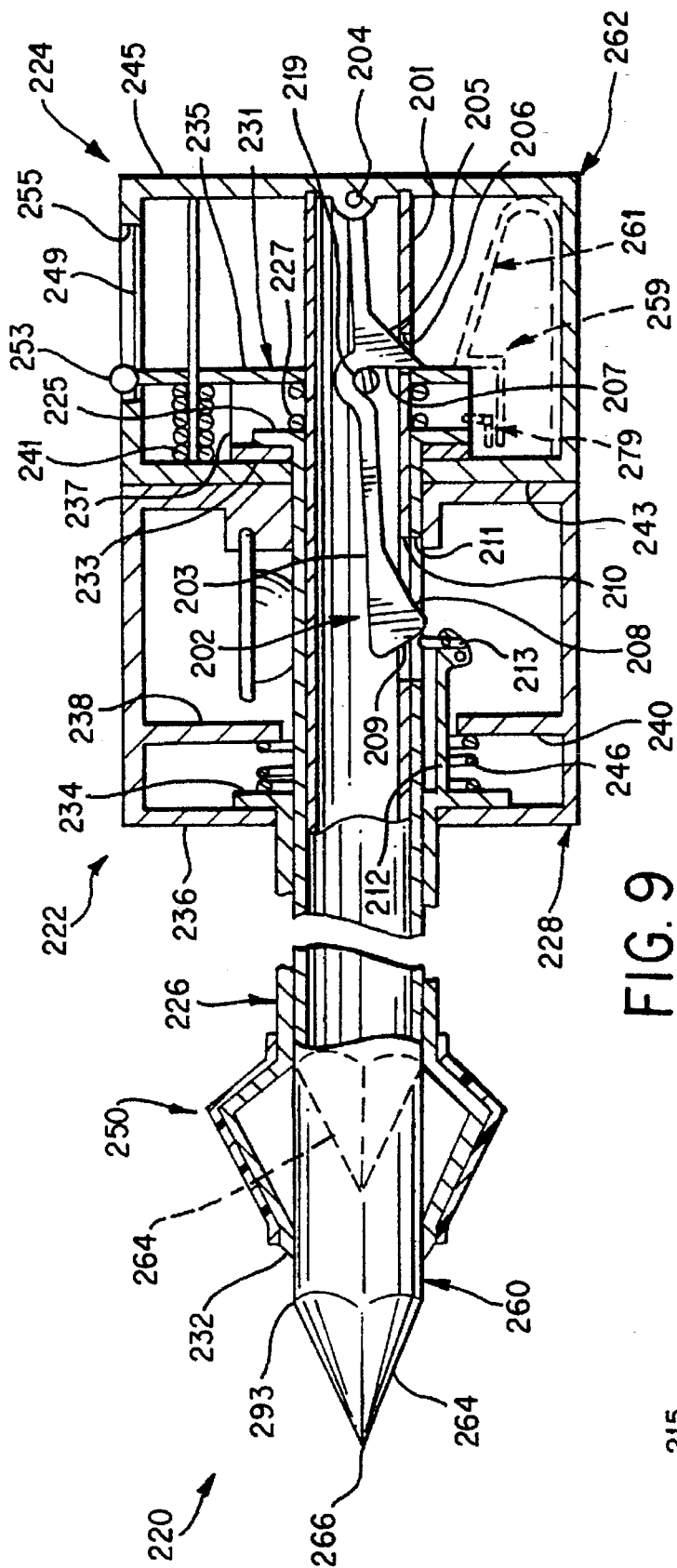
FIG. 9 is a broken side view, partly in section, of another modification of the penetrating instrument according to the present invention.

Release of the penetrating member to move proximally to the retracted position can be triggered by movement of an operating member connected with the penetrating member, the portal sleeve and/or a safety member, such as a shield or probe. In FIG. 9, a modification of the penetrating instrument according to the present invention is illustrated wherein an operating member is carried by the portal sleeve. The modified penetrating instrument 220 is formed of a portal unit 222 similar to portal unit 22 and a penetrating unit 224 similar to penetrating unit 124.

Penetrating unit 224 includes a penetrating member 260, a hub 262 mounting a proximal end of the penetrating member and a modified locking and releasing mechanism 202. Penetrating member 260 is similar to penetrating member 160 and terminates distally at a distal end 264 and proximally at a transverse flange 225 disposed between forward and rearward walls 233 and 235 of a rail member 231. The proximal end of the penetrating member 260 also includes a hollow portion telescopically fitted over a guide tube 201 extending distally from the rear wall 245 of the hub. The bias member 227 is similar to bias member 127 and is disposed around the guide tube 201 and held in compression between the penetrating member flange 225 and the rearward wall 235 of rail member 231. A retracting member 241, similar to retracting member 141, is disposed around the penetrating member and is held in compression between the rail member rearward wall 235 and hub front wall 243.

The penetrating member 260 is locked in the extended position shown in FIG. 9 by a modified locking and releasing mechanism 202 having a longitudinal latch arm 203 disposed within the guide tube 201 and having a proximal end pivotally mounted on a pin 204 secured to the rear wall of the hub. Latch arm 203 carries or forms a latching protrusion 205 in opposed relation to a slot 206 formed in the guide tube. Protrusion 205 is generally triangular with a transverse latching surface 207 configured to extend through slot 206 formed in the guide tube to engage the rail member rearward wall 235. A torsion spring or other type or spring or bias device (not shown) is connected between the latch arm 203 and the pin or guide tube to bias the arm in a counterclockwise direction looking at FIG. 9 toward an engaged position where latching protrusion 205 extends through the slot 206 formed in the guide tube. A triggering protrusion 208 is formed at a distal end of the latch arm 203 and includes an angled distal edge or surface 209 that protrudes through aligned slots 210 and 211 formed in the guide tube and the penetrating member distally of slot 206 to communicate into the housing 228. Penetrating member slot 211 is sufficiently long to allow back and forth movement of the penetrating member 260 within the rail member 231 during penetration of an anatomical cavity wall.

A control button 219 extends through the hub 262 to be disposed adjacent a lower edge of latch arm 203 looking at FIG. 9. The control button 219 has a tapered or wedge-shaped surface that contacts the lower edge of the latch arm 203 and an exterior portion (not shown). Depression of the exterior portion of the control button 219 causes the tapered or wedge-shaped portion of the button to cam the latch arm 203 inwardly in the clockwise direction looking at FIG. 9 so that the triggering and latching protrusions 208 and 205 are disposed within the guide tube to facilitate insertion of the penetrating member 260 into the portal unit 222 and/or to manually disengage the locking and releasing mechanism.

Figure 9A:
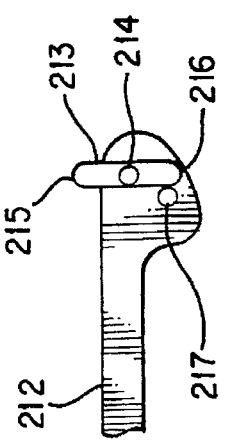
FIG. 9A is an enlarged fragmentary side view of a trigger lever for the penetrating instrument of FIG. 9.

Portal unit 222 is similar to portal unit 22 for safety penetrating instrument 20 and, in addition, includes a finger 212 extending perpendicularly from the portal sleeve flange 234 in a proximal direction and a lever 213 mounted at the proximal end of finger 212 near triggering protrusion 208. Finger 212 extends through an opening formed between interior wall 240 and penetrating member 260 and terminates proximally in a barb or pawl with a proximal leading edge angled inwardly and a vertical trailing edge. As best seen in FIG. 9A, lever 213 is pivotally mounted on a pin 214 secured to finger 212 and includes axially opposed upper and lower ends 215 and 216. A post or peg 217 is mounted on the finger 212 adjacent the lower end 216 of the lever to serve as a stop limiting clockwise rotation of the lever beyond a transverse position where the lever is oriented substantially perpendicular to the longitudinal axis of the penetrating instrument. In the transverse position, upper end 215 of the lever is in the longitudinal path of triggering protrusion 208. A torsion spring or the like (not shown) biases the lever in the clockwise direction into contact with peg 217 while permitting counterclockwise rotation of the lever in response to a distal force acting on upper end 215.

Use of the safety penetrating instrument 220 is similar to that described above with respect to safety penetrating instrument 120 in that, when the user desires to penetrate into an anatomical cavity, the safety penetrating instrument will normally be provided with the penetrating member 260 in the retracted position, shown by dotted line in FIG. 9, where the distal end 264 of the penetrating member is proximally spaced from the portal sleeve distal end 232. Additionally, the portal sleeve 226 will be provided in the rest position where the portal sleeve flange 234 abuts the housing front wall 236 and the expandable portion 250 of the portal sleeve is in the expanded position. Furthermore, latching protrusion 205 of latch arm 203 will be disposed distally of the rail member rearward wall 235 and lever 213 will be disposed distally of triggering protrusion 208. The penetrating member 260 is biased to the retracted position by retracting member 241 with handle 253 being disposed at a proximal end of the slot 249 in the hub 262.

Prior to commencing penetration of an anatomical cavity wall, handle 253 is grasped and manually moved distally to move penetrating member 260 distally against the bias of retracting member 241 until the rail member rearward wall 235 rides over the latching protrusion 205 by engaging an angled proximal surface of the latching protrusion to move the latch arm 203 clockwise looking at FIG. 9. When rail member rearward wall 235 moves distally past latching surface 207, latch arm 203 springs back in a counterclockwise direction to lock the rail member 231 and penetrating member 260 mounted thereby in the extended position shown. As previously noted, the user can feel the rail member lock into place in engagement with latch arm 203 and can also visually determine that the penetrating member is in the locked extended position by noting the position of the handle 253 at a distal end of the slot. With the penetrating member 260 locked in the extended position, penetrating member flange 225 will be distally biased by bias member 227 into abutting relation with the rail member forward wall 233, and the portal sleeve flange 234 will be distally biased by bias member 246 into abutment with housing forward wall 236 such that the distal end 232 of the portal sleeve will be proximally spaced from the transverse dimensional transition or junction 293 at the distal end of the penetrating member a predetermined distance corresponding to the axial extension of expandable portion 250 caused by movement of the expandable portion from the extended position to the contracted position.

With the safety penetrating instrument 220 in the position illustrated in FIG. 9, penetration of the anatomical cavity wall is commenced, and the force from tissue contact on the portal sleeve and penetrating member distal ends 232 and 264 will cause the portal sleeve and penetrating member to move together proximally against the bias of springs 246 and 227, respectively. Proximal movement of the portal sleeve 226 also causes the operating member formed by the upper end 215 of lever 213 to contact and move past triggering protrusion 208. Lever upper end 215 is rotated counterclockwise in response to contact with triggering protrusion 208 without causing any movement of latch arm 203. Lever 213 is biased in the clockwise direction; and, accordingly, when lever upper end 215 is positioned proximally of the triggering protrusion the lever will assume its transverse position. Upon entry into the anatomical cavity, the force from tissue contact on the distal end of the portal sleeve will be lessened, reduced or removed allowing spring 246 to move the portal sleeve distally causing lever upper end 215 to engage triggering protrusion 208. Lever 213 is prevented from rotating clockwise by engagement of lever lower end 216 with post 217 so that lever upper end 215 will cam the triggering protrusion 208 into the guide tube causing the latch arm 203 to pivot clockwise looking at FIG. 9. Clockwise pivotal movement of latch arm 203 causes the latching protrusion 205 to move out of engagement with rail member rearward wall 235 thereby allowing retracting member 241 to move the penetrating member proximally to the retracted position, shown by dotted lines in FIG. 9, wherein the penetrating member distal end 264 is proximally spaced from the distal end 232 of the portal sleeve 226 to protect tissue and organ structures from the sharp tip 266 of the penetrating member. At about the same time, expandable portion 250 will enter the anatomical cavity and, as a result of the reduction in force from tissue contact, the expandable portion 250 will return to the expanded position within the anatomical cavity. Once expandable portion 250 has moved from the contracted position to the expanded position upon penetration into the anatomical cavity, the instrument can be pulled back toward the cavity wall until the enlargement formed by expandable portion 250 is adjacent or in abutment with an internal surface of the cavity wall at which time the portal sleeve will be anchored relative to the anatomical cavity wall to prevent backing out of the portal sleeve from the anatomical cavity. The penetrating unit 224 can then be withdrawn from the portal unit 222 leaving the portal sleeve 226 in place for the introduction of medical instruments therethrough.

Another modification of the safety penetrating instrument of the present invention is arrived at by combining the locking and releasing mechanisms of safety penetrating instruments 120 and 220 to permit movement of the penetrating member to the retracted position in response to a distally-biased movement of both the portal sleeve and the penetrating member. The modification involves mounting a locking and releasing mechanism, such as locking and releasing mechanism 159, for engaging the rail member 231 in hub 262 of penetrating instrument 220, as shown by dotted lines at 259 in FIG. 9. Use of the modified penetrating instrument is similar to that described above in connection with penetrating instruments 120 and 220 with the exception that both the latch spring 261 and latch arm 203 must be disengaged in order for the penetrating member 260 to be moved proximally to the retracted position.

Figure 10:
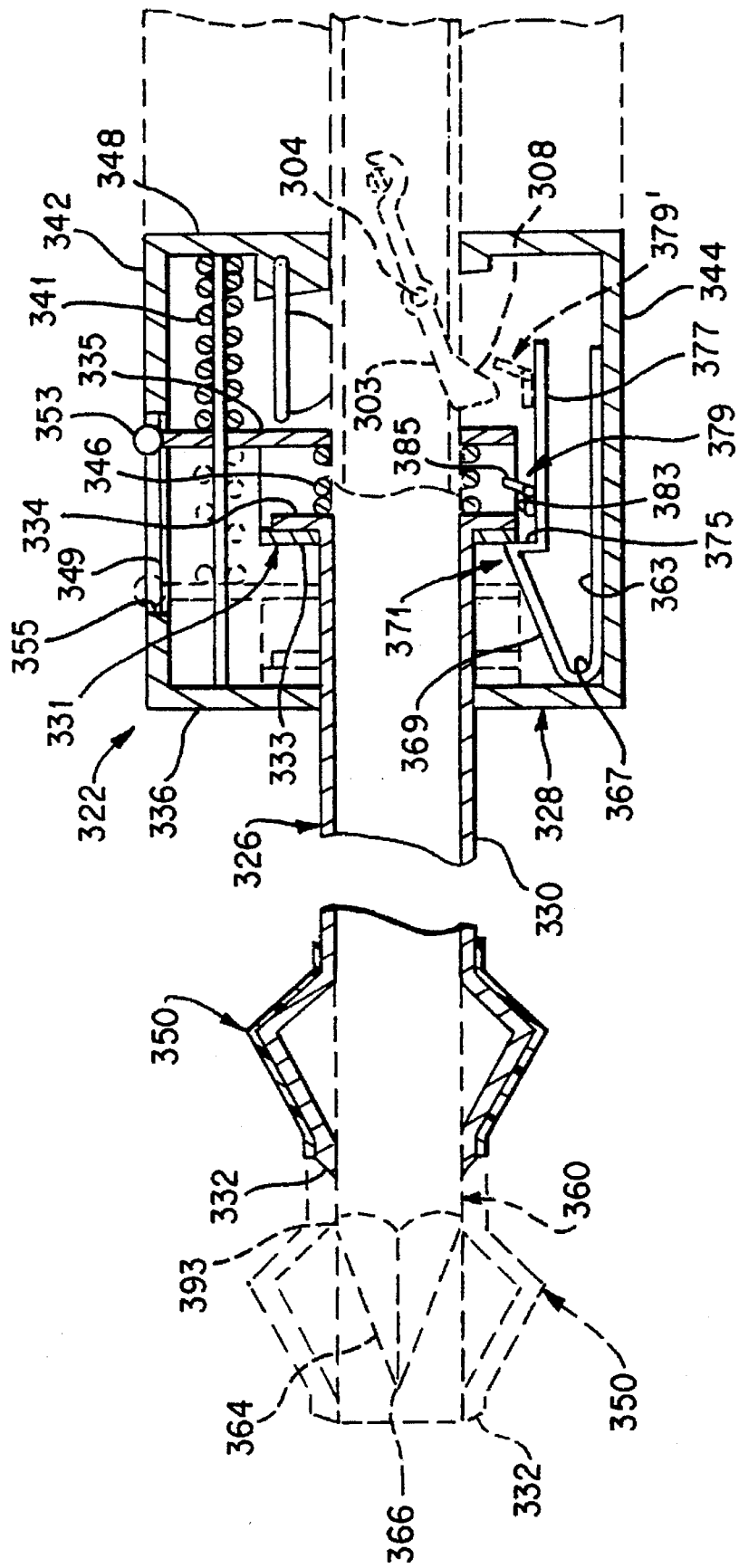
FIG. 10 is a broken side view, partly in section, of yet another modification of the penetrating instrument according to the present invention.

The portal sleeve of the penetrating instrument according to the present invention can be fixed or movable relative to the housing; and, when the portal sleeve is movable relative to the housing, the portal sleeve can function as a "safety member" to protrude distally beyond the penetrating member tip preventing contact between the tip and anatomical tissue and organ structures. FIG. 10 illustrates a further modification of the penetrating instrument according to the present invention where, in addition to carrying an expandable portion, the portal sleeve functions as a triggered safety member to protect the distal tip of the penetrating member. Only the portal unit 322 of the modified penetrating instrument 320 is shown in FIG. 10; it will be appreciated, however, that any of the penetrating units described herein can be coupled with the modified portal unit 322 depending on procedural use and the desirability of having a fixed or retractable penetrating member and/or a separate safety shield in conjunction with the portal sleeve safety member.

The modified portal unit 322 is made up of portal sleeve 326 and housing 328. Portal sleeve 326 is similar to portal sleeve 226 for safety penetrating instrument 220 except that portal sleeve 326 terminates proximally at a flange 334 disposed between forward and rearward walls 333 and 335 of a rail member 331 disposed in housing 328 with the portal sleeve passing through an opening in the rail member forward wall and a bias member 346 being held in compression between flange 334 and rail member rearward wall 335 to bias the portal sleeve distally relative to the rail member. Like rail member 231, rail member 331 is generally U-shaped and includes a forward wall 333 disposed transverse or perpendicular to a longitudinal axis of the safety penetrating instrument, a rearward wall 335 parallel to forward wall 333 and a side wall 337 joining the rail member forward and rearward walls. An extending member 341 is connected between the housing rear wall 348 and the rail member 331 to bias the rail member and, therefore, the portal sleeve 326, distally to a portal sleeve or safety member extended position. Extending member 341 can include various tension springs, compression springs, pan springs, torsion springs, rubber, plastic or magnets, for example, or any other bias device. As shown in FIG. 10, the extending member 341 can include a helical coil spring held in compression between the housing rear wall 348 and the rearward wall 335 of the rail member.

The locking and releasing mechanism 359 for locking the portal sleeve 326 in a portal sleeve or safety member retracted position where the distal end 332 of the portal sleeve is disposed proximally of penetrating member sharp tip 366 with the penetrating member in the penetrating member extended position and for releasing the portal sleeve to move to the portal sleeve or safety member extended position where distal end 332 is disposed distally of tip 366 includes a latch or locking spring 371 disposed in housing 328 and made of a strip of resilient material formed to have a substantially flat base 363 secured to a lower wall 344 of housing 328 or supported by structure in the housing and a bend 367 joining a distal end of base 363 with an upwardly angled arm 369 spaced from the base. Arm 369 has an extension 377 disposed substantially parallel with the instrument longitudinal axis and carries or forms a latch 371 having an angled proximal latching surface 375 extending inwardly from extension 377 in a direction transverse or perpendicular to the longitudinal axis of the instrument and disposed substantially parallel with the rail member forward wall 333. A releasing or trigger member 379 is juxtaposed with extension 377 and is pivotally mounted in the housing 328 on a pin secured to a wall or walls of the housing or structure in the housing. Trigger 379 includes a leg 383 overlying extension 377 and a leg 385 extending substantially transverse from leg 383 but at a slight angle toward the proximal end of the safety penetrating instrument. A torsion spring (not shown) is coiled around the pin and fixed to trigger 379 to bias the trigger counterclockwise looking at FIG. 10 such that leg 383 is biased toward extension 377. Trigger 379 is arranged in housing 328 with leg 385 disposed in the path of longitudinal movement of portal sleeve flange 334.

In use, portal unit 322 will normally be supplied with the portal sleeve 326 in the extended position shown by dotted lines in FIG. 10 and will be coupled with a penetrating unit prior to use in penetrating an anatomical cavity wall. In the extended position, portal sleeve distal end 332 will protrude distally beyond the sharp tip 366 of the penetrating member 360 and expandable portion 350 will be in the expanded position.

Prior to commencing penetration of an anatomical cavity wall W, the portal sleeve 326 is moved from the portal sleeve extended position to the portal sleeve retracted position by grasping handle 353 and sliding the handle in a proximal direction along slot 349. Proximal movement of handle 353 causes rail member 331 to be moved proximally until rail member forward wall 333 rides over latch 371. Once the rail member forward wall has moved proximally past latch 371, arm 369 of locking spring 361 will spring back to the normal position illustrated in FIG. 10 causing rail member forward wall 333 to be locked against latching surface 375. At this time, the portal sleeve 326 will be locked in the portal sleeve retracted position with distal end 332 disposed proximally of sharp tip 366 of the penetrating member. With the portal sleeve locked in the portal sleeve retracted position, expandable portion 350 will remain in the expanded position and the operating member formed by flange 334 will be biased to abut rail member forward wall 333 and thereby be disposed distally of trigger leg 385.

During penetration of the anatomical cavity wall W, portal sleeve 326 will be moved proximally in response to the force from tissue contact with the distal end of the portal sleeve and expandable portion 350 will be moved from the expanded position shown to the contracted position. Proximal movement of the portal sleeve 326 causes the operating member formed by flange 334 to move proximally past trigger leg 385 without causing movement of latch 371 since there is no engagement by either leg 383 or 385 with arm extension 377. Accordingly, during penetration of the anatomical cavity wall, the portal sleeve 326 remains locked in the portal sleeve retracted position by latch 371.

Once the expandable portion 350 has been introduced in the anatomical cavity, the expandable portion will move from the contracted position to the expanded position. At about the same time, the portal sleeve and, thus, the operating member formed thereby, are moved distally to engage trigger leg 385 causing the trigger 379 to pivot or rotate counterclockwise looking at FIG. 10 and causing leg 383 to engage arm extension 377 moving arm 369 toward base 363 against the force of the spring strip. Movement of arm 369 away from the longitudinal axis of the safety penetrating instrument causes latch 371 to move out of engagement with rail member forward wall 333 thereby allowing extending member 341 to move the portal sleeve 326 in a distal direction to the portal sleeve extended position where distal end 332 of the portal sleeve will be disposed distally of the sharp tip of a penetrating member. Once the expandable portion is moved to the expanded position, the instrument can be pulled back toward the cavity wall until the expandable portion is adjacent or in abutment with an internal surface of the anatomical cavity wall. The enlargement formed by the expandable portion will anchor the portal sleeve relative to the anatomical cavity, and the portal sleeve will be anchored to protrude into the anatomical cavity a distance corresponding to the distance from the portal sleeve distal end to a proximal end of the expandable portion.

Another modification of the penetrating instrument of the present invention is arrived at by coupling the portal unit 322 with a penetrating unit 324 having a penetrating member 326 with a pivotable protrusion 308 extending therefrom as shown by dotted line in FIG. 10. The protrusion 308 is formed at one end of an arm 303 mounted within the penetrating member on a pin 304. An opposite end of the arm forms a concave pocket 318 to accommodate a tapered or wedge-shaped button 319 that extends from outside the hub of the penetrating unit through the pocket. Depression of button 319 into the housing causes the button to wedge itself against arm 303 rotating the arm clockwise and drawing protrusion 308 toward the interior of the penetrating member to ease insertion of the penetrating member into the portal unit. Arm 303 is biased counterclockwise looking at FIG. 10 so that, when button 319 is withdrawn or released, protrusion 308 will pivot into the housing to serve as an operating member for engaging a second trigger member 379' proximally spaced from trigger member 379. It will be appreciated, therefore, that the aforementioned penetrating instrument provides redundant protection against inadvertent contact with tissue or organ structures in or forming an anatomical cavity with the sharp tip of the penetrating member by triggering protrusion of the portal sleeve safety member in response to distally-biased movement of either or both of the portal sleeve and the penetrating member. Furthermore, if the penetrating member is retractable, two modes of safety are provided: retraction of the penetrating member and protrusion of the safety member, ensuring that the sharp tip of the penetrating member will be protected even if one of the modes of safety malfunctions.

The penetrating instruments described thus far have each included a portal sleeve carrying an expandable portion and a penetrating member disposed within the portal sleeve. It will be appreciated, however, that a tubular safety shield could be disposed between the penetrating member and the portal sleeve of any of the penetrating instruments described herein to serve as a safety member that is distally biased to an extended protruding position protecting the distal tip of the penetrating member and/or to trigger retraction of the penetrating member or protrusion of other safety members. The penetrating instrument illustrated at 420 in FIG. 11, for example, includes a penetrating unit 424 having a safety shield 497, a penetrating member 460 disposed within the safety shield and a hub 462 mounting proximal ends of the penetrating member and the safety shield. Safety shield 497 is shown as an elongate hollow cylinder but can have any configuration to fit between the penetrating member and the portal sleeve. The safety shield terminates distally at a distal end 498 and proximally at a transverse flange 499 disposed between walls of a rail member 431 mounted in hub 462. A protrusion 408 extends outwardly from the safety shield in a lateral direction substantially perpendicular to the longitudinal axis of the penetrating instrument at a location intermediate the proximal and distal ends of the safety shield to be disposed within housing 428 of the penetrating instrument when the penetrating unit 424 is coupled with the portal unit 422. Protrusion 408 is made of a tongue of material or tang cut from the body of the safety shield and is formed to have a distal surface 409a extending outwardly in a transverse direction from the safety shield and a proximal surface 409b extending inwardly at an angle from the transverse distal surface 409a toward a proximal end of the instrument. The protrusion is designed to resiliently deform or collapse when passed through an opening in the rear wall of the housing when the portal and penetrating units are assembled and to regain its extended shape once inside the housing. Alternatively, protrusion 408 could be formed by a strip of material separating a pair of spaced slots formed in the safety shield or by a pivotable arm mounted within the penetrating member and made to pass through openings in the penetrating member and safety shield to be disposed within the housing.

Rail member 431 has a generally U-shaped configuration with spaced, parallel forward and rearward walls 433 and 435, respectively, and a side wall 437 transversely connecting the forward and rearward walls. Flange 499 is disposed between the rail member forward and rearward walls 433 and 435 with the safety shield passing through aligned openings in a forward wall of hub 462 and rail member forward wall 433. Penetrating member 460 extends distally from a rear wall of hub 462 through an opening in the rail member rearward wall 435 and into a proximal end of safety shield 497. A bias member 427 is connected between flange 499 and the rearward wall 435 of the rail member to bias the safety shield in a distal direction with flange 499 biased in abutment with rail member forward wall 433. Bias member 427 is shown as a helical coil spring disposed around the penetrating member and held in compression between flange 499 and rearward wall 435; however, bias member 427 can include other types of springs as well as other types of bias devices as described previously. An extending member 441 is connected between rail member rearward wall 435 and a front wall of hub 462 to bias the safety shield distally to an extended position where the distal end 498 of the safety shield protrudes distally beyond the penetrating member distal end 464. As shown, the extending member 441 includes a helical coil spring disposed around a guide rod and held in tension between the rail member rearward wall and the front wall of the hub. A pin or post 447 extends upward from rail member rearward wall 435 through a longitudinal slot 449 formed in the upper wall 439 of the hub to terminate at a knob 453 disposed within an elongate, trough-like recess 455.

A locking and releasing mechanism 459 for locking the safety shield in the safety shield retracted position and for releasing the safety shield to move to the safety shield extended position is disposed in hub 462 and includes a latch or locking spring 461 made of a strip of resilient material formed to have a substantially flat base 463 secured to a wall of hub 462 and a bend 467 joining the distal end of the base 463 with an upwardly angled arm 469 spaced from the base. Arm 469 carries or forms a latch 471 having a proximal latching surface 475 disposed substantially parallel to forward wall 433 of rail member 431. Arm 469 has an extension 477 extending proximally from latch 471, and a trigger member 479 is juxtaposed with extension 477. Trigger member 479 is similar to trigger member 379 and includes a trigger leg 483 overlying extension 477 and a trigger leg 485 extending substantially transverse from leg 483 with a slight angle toward the proximal end of the safety penetrating instrument. Trigger 479 is arranged in hub 462 with trigger leg 485 disposed in the path of longitudinal movement of safety shield flange 499 when the flange is moved in response to the force from tissue contact with the distal end of the safety shield.

Portal unit 422 for safety penetrating instrument 420 includes a portal sleeve 426 and a housing 428 mounting a proximal end of the portal sleeve. Portal sleeve 426 carries an expandable portion 450 and terminates proximally at a transverse flange 434 disposed within housing 428. A locking and releasing mechanism 459', similar to locking and releasing mechanism 359, is mounted in the housing to lock the portal sleeve 426 in a retracted position and to release the portal sleeve to be moved to an extended position in response to distally biased movement of the safety shield 497. The locking and releasing mechanism includes a latch or locking spring 461' disposed in housing 428 and made of a strip of resilient material formed to have a substantially flat base 463' secured to a lower wall 444 of housing 428 or supported by structure in the housing and a bend 467' joining a distal end of base 463' with an upwardly angled arm 469' spaced from the base. Arm 469' has an extension 477' disposed substantially parallel with the instrument longitudinal axis and carries or forms a latch 471' having an angled proximal latching surface 475' extending inwardly from extension 477' in a direction transverse or perpendicular to the longitudinal axis of the instrument and disposed substantially parallel with the portal sleeve flange 434. A releasing or trigger member 479' is juxtaposed with extension 477' and is pivotally mounted in the housing 428 on a pin 481' secured to a wall or walls of the housing or structure in the housing. Trigger 479' includes a leg 483' overlying extension 477' and a leg 485' extending substantially transverse from leg 483' but at a slight angle toward the proximal end of the safety penetrating instrument. A torsion spring (not shown) is coiled around the pin and fixed to trigger 479' to bias the trigger counterclockwise looking at FIG. 11 such that leg 483' is biased toward extension 477'. Trigger 479' is arranged in housing 428 with leg 485' disposed in the path of longitudinal movement of safety shield protrusion 408.

Portal sleeve flange 434 extends upward toward the housing upper wall 442 and an extending member 441' is connected between the flange 434 and the rear wall 448 of the housing to bias the portal sleeve in a distal direction to an extended position where a distal end 432 of the portal sleeve protrudes beyond the sharp tip 466 of the penetrating member. Extending member 441' is shown as a helical coil spring held in compression between the flange 434 and the housing rear wall 448 but can be any type of spring or bias device as described above. A post or pin 447' extends upward from the portal sleeve flange 434 through a longitudinal slot 449' formed in the housing upper wall 442 to terminate at a knob or handle 453' disposed within an elongate, trough-like recess 455'.

Operation of safety penetrating instrument 420 is similar to that previously described in that the instrument can be provided with the portal sleeve 426 in either the portal sleeve extended position shown by broken lines in FIG. 11 or the retracted position shown by solid lines, and the safety shield 497 can be provided in either the safety shield extended position shown by broken lines or the safety shield retracted position shown by solid lines. When the instrument 420 is provided with the portal sleeve in the portal sleeve extended position, prior to penetration of an anatomical cavity wall, handle 453' is grasped and manually moved proximally along the slot in housing 428 to move the portal sleeve 426 to the portal sleeve retracted position with portal sleeve flange 434 in engagement with latching surface 475' at which time the portal sleeve will be locked in the portal sleeve retracted position and expandable portion 450 will be in the expanded position. If the safety shield 497 is also supplied in the extended position, the safety shield 497 can be moved to the safety shield retracted position by grasping handle 453 coupled with rail member 431 and manually moving the handle proximally along the slot formed in the hub until rail member forward wall 433 engages proximal latching surface 475 of locking spring 461 within the hub. The instrument will then be in the condition shown in FIG. 11 with portal sleeve 426 locked in the portal sleeve retracted position and safety shield 497 locked in the safety shield retracted position such that the sharp tip 466 of the penetrating member will be disposed distally of portal sleeve distal end 432 and safety shield distal end 498.

During penetration of an anatomical cavity wall, safety shield 497 will be moved proximally against the bias of bias member 427 causing flange 499 to move proximally past trigger leg 485 without causing movement of latch 471 out of engagement with rail member 431 and also causing protrusion 408 to move proximally past trigger leg 485' in the housing without causing movement of latch 471' out of engagement with portal sleeve flange 434. Expandable portion 450 at the distal end of portal sleeve 426 will also be moved from the expanded position shown to the contracted position such that the distal end 432 of the portal sleeve 426 will be moved distally and preferably become axially aligned with the distal end 498 of the safety shield 497 to create a smooth profile easing penetration of the anatomical cavity wall. Upon penetrating into the anatomical cavity, the safety shield 497 will be moved distally due to the bias of bias member 427 causing the operating member formed by flange 499 to engage trigger leg 485 and to pivot trigger member 479 counterclockwise, looking at FIG. 11, such that latch 471 is moved out of engagement with rail member rearward wall 435. Distal movement of the safety shield 497 will also cause protrusion 408 to engage trigger leg 485' and to pivot trigger member 479' counterclockwise such that latch 471' is moved out of engagement with the portal sleeve flange 434. As a result, extending members 441 and 441' will move the safety shield 479 and the portal sleeve 426 to their respective extended protruding positions as shown by broken lines in FIG. 11 to protect tissue and organ structures from the tip 466 of the penetrating member. Expandable portion 450 will also be moved from the contracted position to the expanded position; and, once the expandable portion is moved to the expanded position, the instrument can be pulled back toward the cavity wall until the expandable portion is adjacent or in abutment with an internal surface of the anatomical cavity wall to anchor the portal sleeve relative to the anatomical cavity.

The distal bias of triggering components of the penetrating instrument according to the present invention need only be great enough to produce slight longitudinal movement of any operating members carried by the components past trigger members such that the force-to-penetrate can be minimized. As mentioned previously, the expandable portion can be located at various locations along the portal sleeve to anchor the instrument relative to the anatomical cavity wall to obtain various predetermined distances of protrusion for the portal unit from the anatomical wall. Also, with the penetrating instruments according to the present invention, redundant safety can be achieved in that two modes of safety can be provided, one relying on protrusion of a safety member and the other relying on retraction of the penetrating member to insure that the sharp tip of the penetrating member will be protected upon penetration through the anatomical cavity wall even should one of the safety modes malfunction during use. The safety and reliability of safety penetrating instruments can be further enhanced with the present invention in that separate, independent trigger mechanisms can be provided for releasing the safety member to move to the safety member extended position and for releasing the penetrating member to move to the penetrating member retracted position.

The components of the safety penetrating instrument of the present invention can be made of any suitable, medical grade materials depending upon procedural use and desirability of being disposable for single patient use or sterilizable for reuse. The components can be made of multiple parts of various configurations and materials to reduce costs. The portal unit can have various valves, stopcocks and seals in the housing to control fluid flow therethrough and various adapters to adjust to the size of the instruments inserted through the portal unit. The portal sleeve can be rigid or flexible and transparent or opaque depending on procedural use. Conventional detent mechanisms can be used to connect or lodge the housing with the hub when the portal unit and the penetrating unit are assembled. The safety member can be part of the portal unit or the penetrating unit such that the safety member can remain in place in the anatomical cavity upon withdrawal of the penetrating unit or can be withdrawn with the penetrating unit leaving only the portal sleeve in place to serve as a portal for introducing instruments into the anatomical cavity. The rail members can have various configurations to engage the latches and be released by the triggers and can have configurations to serve as a stop or abutment for the operating members.

The locking and releasing mechanisms require only a latch for locking the penetrating member in the extended position and/or a safety member in a retracted position, and a trigger for releasing the latch in response to distal movement of an operating member such as a flange carried by the penetrating member, the portal sleeve or a safety member; and, thus, it will be appreciated that various mechanisms can be employed to produce the locking and releasing functions such as, for example, multiple movably or pivotally mounted cams or pawls. It will be appreciated that the locking and releasing mechanism can be designed and arranged in the housing or the hub in various ways to minimize the length of the housing or the hub and, therefore, the overall length of the housing and hub. Various locking and releasing mechanisms that can be simply modified for use in the safety penetrating instrument of the present invention are disclosed in U.S. Pat. Nos. 5,330,432; 5,324, 268; 5,320,610; 5,336,176; and 5,360,405 to Yoon and applicant's pending applications Ser. No. 07/848,838, filed Mar. 10, 1992; Ser. No. 07/845,177, filed Sep. 15, 1992; Ser. No. 07/945,177, filed Sep. 15, 1992; Ser. No. 08/079,586, filed Jun. 22, 1993; Ser. No. 08/195,512, filed Feb. 14, 1994; Ser. No. 08/196,029, filed Feb. 14, 1994; Ser. No. 08/196, 027, filed Feb. 14, 1994; Ser. No. 08/195,178, filed Feb. 14, 1994; Ser. No. 08/237,734, filed May 4, 1994; Ser. No. 08/247,205, filed May 20, 1994; Ser. No. 08/254,007, filed Jun. 3, 1994; and Ser. No. 08/260,439, filed Jun. 15, 1994. The disclosures of the above-listed issued patents and pending patent applications are incorporated herein by reference. The issued patents and pending applications listed above also disclose various bias arrangements useful with the safety penetrating instrument of the present invention. Other locking and releasing mechanisms that can be used in the safety penetrating instrument of the present invention are disclosed in applicant's pending applications Ser. Nos. 08/279,170 and 08/279,172, filed Jul. 22, 1994, the disclosures of which are incorporated herein by reference.

One or more control buttons, such as the control buttons described in applicant's copending patent application, Ser. No. 08/083,220, filed Jun. 24, 1993, can be mounted next to any latch for manually disengaging the latch to prevent locking of the penetrating member in the extended position and/or a safety member such as the portal sleeve in a retracted position. Furthermore, additional latches can be provided or existing latches modified to carry pawls or form latching surfaces for locking a penetrating member in the retracted position and/or a safety member in the extended position, and such latches can then be released through the use of control buttons as described above to permit the penetrating member and/or safety member to be moved prior to use.

Figure 12:
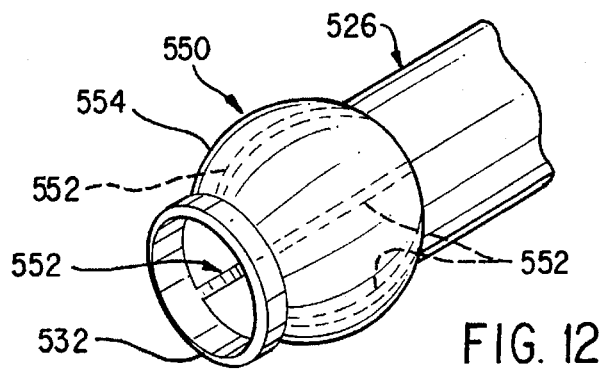
FIG. 12 is a fragmentary perspective view of a modified expandable portion formed at the distal end of a portal sleeve of the penetrating instrument according to the present invention.

It will be appreciated that the expandable portion can be configured in many various ways to form an enlargement or protrusion having a configuration to anchor the portal sleeve relative to an anatomical cavity. Accordingly, the strips shown herein can form an angularly shaped enlargement as described above or spherical, toroidal or doughnut shaped enlargements. In FIG. 12, for example, a modified expandable portion 550 is shown having curved strips 552 forming a spheroidal enlargement. The expandable portion could also be formed as an inflatable membrane, and the expandable portion can be used with or without the protective membrane or sheath.

Figure 13:
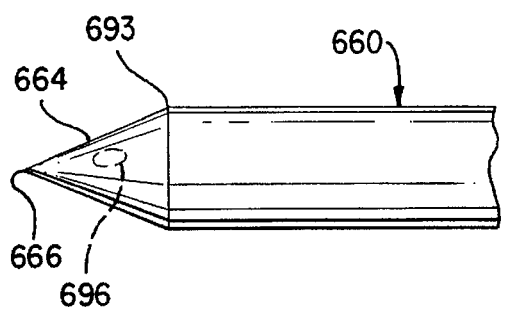
FIGS. 13–18 are fragmentary side views of modified penetrating members for the penetrating instrument of the present invention.
Figure 14:
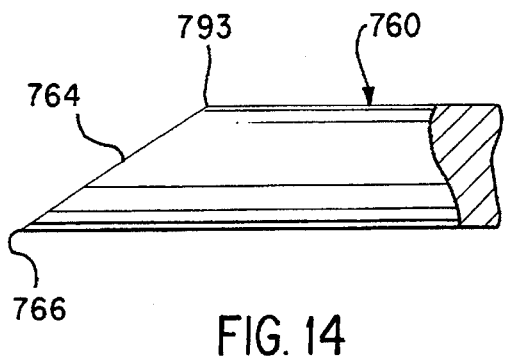
Figure 15:
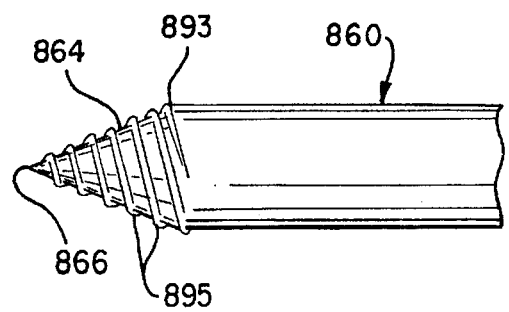
Figure 16:
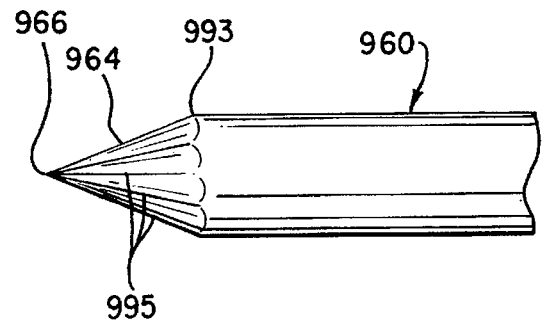
Figure 17:
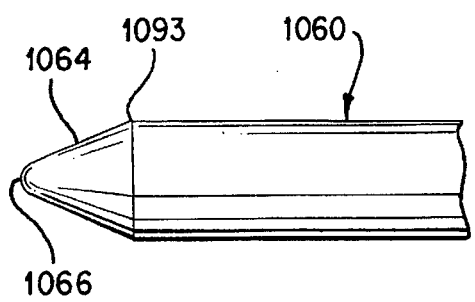
Figure 18:
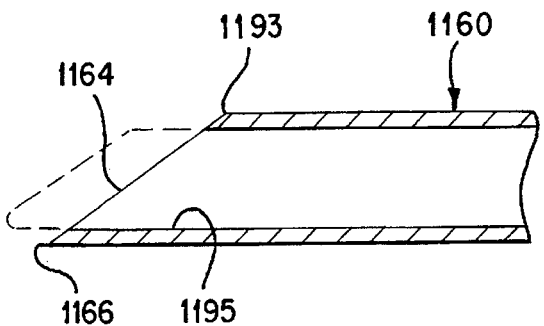

The distal end of the penetrating member for the safety penetrating instrument of the present invention can have any configuration desired for a particular procedure, for example, the pyramidal trocar configuration shown or a conical distal end 664 tapering from a junction 693 to a tip 666 as shown in FIG. 13, a beveled distal end 764 tapering from a junction 793 to a tip 766 as shown in FIG. 14, a screw-type distal end 864 having helical threads 895 as shown in FIG. 15, a multi-faceted distal end 964 having two or more facets 995 tapering from a junction 993 to a tip 966 as shown in FIG. 16, a blunt distal end 1064 of generally conical configuration terminating in a rounded or flattened tip 1066 as shown in FIG. 17, or a hollow tubular needle-like configuration with a beveled distal end 1164 tapering from a junction 1193 to a sharp tip 1166 and defining a lumen 1195 to permit the flow of fluid therethrough and/or to accommodate a safety probe disposed therein as shown by broken line in FIG. 18. Additionally, the surface defining the distal end of the penetrating member can be irregular or smooth, continuous or disjointed, provided with cutting features or having any combination of the above. Any of the penetrating members shown and described herein can include a viewing port, like the viewing port shown in phantom at 696 in FIG. 13, for accommodating conventional optical viewing systems such as those utilizing fiber optics so that tissue can be visualized during penetration. It will also be appreciated that the distal end of the portal sleeve can be proximally spaced, distally spaced or aligned with the penetrating member junction from which the distal end extends prior to penetrating an anatomical cavity wall, for example when the penetrating member is locked in an extended position and/or the portal sleeve is locked in a retracted position.

From the above, it will be appreciated that the penetrating instrument of the present invention allows the distal end of a portal sleeve to be automatically anchored relative to an anatomical cavity wall without intervention by a surgeon and without requiring complex mechanisms or parts. With the penetrating instrument of the present invention, automatic anchoring is achieved through the use of an expandable portion movable between expanded and contracted positions in response to resistance from anatomical tissue during penetration of an anatomical cavity wall and a reduction in tissue resistance following entry into the anatomical cavity. The features of the various embodiments described above can be combined in any manner desired dependent upon the requirements and complexity of the penetrating instruments.

Inasmuch as the present invention is subject to many variations, modifications and changes in detail, it is intended that all subject matter discussed above or shown in the accompanying drawings be interpreted as illustrative only and not be taken in a limiting sense.

What is claimed is:

1. A penetrating instrument for penetrating an anatomical cavity wall to gain access to an anatomical cavity comprising
    a cannula having a distal end for being disposed in the anatomical cavity and a proximal end for being disposed externally of the anatomical cavity;
    a penetrating member disposed in said cannula and having a distal end for penetrating the anatomical cavity wall; and
    an expandable portion disposed along said cannula a predetermined distance from said cannula distal end, said expandable portion being biased outwardly in a lateral direction transverse to a longitudinal axis of said cannula to an expanded position and being movable to a contracted position against said bias in response to tissue resistance during penetration of the anatomical cavity wall, said expandable portion further being movable from said contracted position to said expanded position in response to a reduction in tissue resistance upon introduction of said expandable portion in the anatomical cavity to anchor said cannula to protrude into the anatomical cavity a distance corresponding to said predetermined distance.

2. A penetrating instrument as recited in claim 1 wherein said expandable portion includes a plurality of strips extending longitudinally along said cannula and biased in a direction transverse to said longitudinal axis to be disposed outwardly of said cannula in said expanded position.

3. A penetrating instrument as recited in claim 2 wherein said strips are curved in said expanded position.

4. A penetrating instrument as recited in claim 2 wherein said strips include straight segments pivotally connected to one another and said segments are pivoted outwardly of said cannula in said expanded position.

5. A penetrating instrument as recited in claim 2 and further comprising a flexible membrane disposed over said strips.

6. A penetrating instrument as recited in claim 2 wherein said penetrating member distal end extends from a junction and said cannula distal end is axially aligned with said junction when said expandable portion is in said contracted position.

7. A penetrating instrument as recited in claim 6 wherein said cannula is movable relative to said penetrating member between an extended position where said cannula distal end protrudes distally from said penetrating member distal end to protect said penetrating member distal end and a retracted position where said cannula distal end is disposed proximally of said penetrating member distal end to expose said penetrating member distal end, and further comprising bias means for biasing said cannula in a distal direction toward said extended position.

8. A penetrating instrument as recited in claim 6 wherein said proximal end of said cannula is fixed relative to said penetrating member.

9. A penetrating instrument as recited in claim 1 and further comprising
    a safety member having a distal end and being movable relative to said penetrating member between an extended position where said safety member distal end protrudes distally from said penetrating member distal end to protect said penetrating member distal end and a retracted position where said safety member distal end is disposed proximally of said penetrating member distal end to expose said penetrating member distal end;
    extending means for moving said safety member distally to said extended position and for permitting said safety member to move proximally to said retracted position;
    handle means coupled with said safety member for manually moving said safety member proximally to said retracted position;
    locking means for locking said safety member in said retracted position during penetration of the anatomical cavity wall; and
    releasing means responsive to penetration of said penetrating instrument into the anatomical cavity for triggering release of said locking means to permit said extending means to move said safety member to said extended position.

10. A safety penetrating instrument as recited in claim 9 wherein said safety member includes an operating member and said releasing means is responsive to distally-biased movement of said operating member for triggering release of said locking means.

11. A safety penetrating instrument as recited in claim 10 wherein said safety member includes said cannula.

12. A safety penetrating instrument as recited in claim 10 wherein said safety member includes a tubular shield disposed between said penetrating member and said cannula.

13. A safety penetrating instrument as recited in claim 9 and further comprising bias means for biasing said penetrating member distally, wherein said penetrating member includes an operating member and said releasing means is responsive to distally-biased movement of said operating member for triggering release of said locking means.

14. A safety penetrating instrument as recited in claim 9 wherein said cannula distal end is axially aligned with said safety member distal end when said expandable portion is in said contracted position.

15. A safety penetrating instrument as recited in claim 1 wherein said penetrating member is movable relative to said cannula between an extended position where said distal end of said penetrating member protrudes distally from said distal end of said cannula and a retracted position proximally spaced from said extended position, and further comprising retracting means for moving said penetrating member proximally from said extended position to said retracted position and for permitting said penetrating member to move distally to said extended position;

handle means coupled with said penetrating member for manually moving said penetrating member distally to said extended position;

locking means for locking said penetrating member in said extended position during penetration of the anatomical cavity wall; and releasing means responsive to penetration of said penetrating instrument into the anatomical cavity for triggering release of said locking means to permit said retracting means to move said penetrating member to said retracted position.

16. A safety penetrating instrument as recited in claim 15 and further comprising bias means for biasing said penetrating member distally in said extended position, wherein said penetrating member includes an operating member and said releasing means is responsive to distally-biased movement of said operating member for triggering release of said locking means.

17. A safety penetrating instrument as recited in claim 15 and further comprising bias means for biasing said cannula distally, wherein said cannula includes an operating member and said releasing means is responsive to distally-biased movement of said operating member for triggering release of said locking means.

18. A safety penetrating instrument as recited in claim 15 and further comprising a safety shield disposed between said cannula and said penetrating member and bias means for biasing said safety shield distally, wherein said safety shield includes an operating member and said releasing means is responsive to distally-biased movement of said operating member for triggering release of said locking means.

19. A safety penetrating instrument as recited in claim 15 wherein said penetrating member distal end extends from a junction and said cannula distal end is axially aligned with said junction when said penetrating member is in said extended position and said expandable portion is in said contracted position.

* * * * *